US008961725B2

(12) United States Patent
Koetse et al.

(10) Patent No.: US 8,961,725 B2
(45) Date of Patent: Feb. 24, 2015

(54) COMPONENT PLACEMENT ON FLEXIBLE AND/OR STRETCHABLE SUBSTRATES

(75) Inventors: Marinus Marc Koetse, Eindhoven (NL); Harmannus Franciscus Maria Schoo, Eersel (NL); Margaretha Maria De Kok, Eindhoven (NL)

(73) Assignee: Nederlandse Organisatie voor toegepast-natuurwetenschappelijk onderzoek TNO, Delft (NL)

( * ) Notice: Subject to any disclaimer, the term of this patent is extended or adjusted under 35 U.S.C. 154(b) by 214 days.

(21) Appl. No.: 13/577,735

(22) PCT Filed: Feb. 9, 2011

(86) PCT No.: PCT/NL2011/050092
§ 371 (c)(1),
(2), (4) Date: Sep. 14, 2012

(87) PCT Pub. No.: WO2011/099851
PCT Pub. Date: Aug. 18, 2011

(65) Prior Publication Data
US 2013/0133822 A1 May 30, 2013

(30) Foreign Application Priority Data
Feb. 9, 2010 (EP) .................................... 10153105

(51) Int. Cl.
*B44C 1/17* (2006.01)
*B29C 65/16* (2006.01)
(Continued)

(52) U.S. Cl.
CPC ............ *H05K 13/0023* (2013.01); *H01L 25/50* (2013.01); *H05K 3/303* (2013.01);
(Continued)

(58) Field of Classification Search
USPC ................ 156/230, 233, 235, 238, 239, 241, 156/247–250, 257, 258, 268, 289, 701, 712, 156/719
See application file for complete search history.

(56) References Cited

U.S. PATENT DOCUMENTS 5,217,550 A * 6/1993 Takeuchi et al. ................ 156/64
5,639,693 A 6/1997 Koseki et al.
(Continued)

FOREIGN PATENT DOCUMENTS

EP 0629110 A2 12/1994
EP 1746869 A1 1/2007
(Continued)

OTHER PUBLICATIONS

International Search Report—PCT/NL2011/050830—Mailing Date: Feb. 27, 2012.
(Continued)

*Primary Examiner* — Sing P Chan
(74) *Attorney, Agent, or Firm* — Banner & Witcoff, Ltd.

(57) ABSTRACT

A method of placement of a component on a stretchable substrate is described. A base substrate, having a stretchable substrate layer, and a flexible foil, having an integral arrangement of multiple flexible foil components, are aligned, so as to be used in a reel based manufacturing process. Through lamination of the base substrate and the flexible foil an electro/optical via connection between in plane interconnecting traces on the stretchable substrate layer and component pads of the integral component arrangement is provided. The integral arrangement of flexible foil components are mechanically separated. The method may be used in a manufacturing process for multi-foil systems.

11 Claims, 9 Drawing Sheets

(51) Int. Cl.
*B32B 37/06* (2006.01)
*B32B 38/10* (2006.01)
*B32B 43/00* (2006.01)
*H05K 13/00* (2006.01)
*H01L 25/00* (2006.01)
*H05K 3/30* (2006.01)
*H05K 3/32* (2006.01)
*H01L 23/00* (2006.01)
*H05K 1/02* (2006.01)
*H01L 25/065* (2006.01)
*H05K 1/18* (2006.01)
*H05K 3/10* (2006.01)

(52) U.S. Cl.
CPC ............... *H05K 3/32* (2013.01); *H01L 24/29* (2013.01); *H01L 24/83* (2013.01); *H05K 1/0283* (2013.01); *H01L 25/0655* (2013.01); *H05K 1/189* (2013.01); *H05K 3/105* (2013.01); *H05K 3/323* (2013.01); *H05K 2201/0133* (2013.01); *H05K 2203/1545* (2013.01); *H01L 2924/01029* (2013.01); *H01L 24/27* (2013.01); *H01L 24/32* (2013.01); *H01L 2224/27505* (2013.01); *H01L 2224/29076* (2013.01); *H01L 2224/29139* (2013.01); *H01L 2224/29147* (2013.01); *H01L 2224/2919* (2013.01); *H01L 2224/2929* (2013.01); *H01L 2224/29393* (2013.01); *H01L 2224/83192* (2013.01); *H01L 2224/83862* (2013.01); *H01L 2224/83874* (2013.01); *H01L 2224/27515* (2013.01); *H01L 2224/32225* (2013.01)
USPC ........... 156/233; 156/238; 156/241; 156/247; 156/249; 156/289; 156/712; 156/719

(56) References Cited

U.S. PATENT DOCUMENTS

| | | | |
|---|---|---|---|
| 5,667,884 A | 9/1997 | Bolger | |
| 6,210,771 B1 | 4/2001 | Post et al. | |
| 6,476,314 B2 * | 11/2002 | Bauman et al. | 136/256 |
| 6,887,650 B2 * | 5/2005 | Shimoda et al. | 430/311 |
| 8,217,566 B2 | 7/2012 | Herrman | |
| 2002/0134422 A1 | 9/2002 | Bauman et al. | |
| 2003/0022403 A1 | 1/2003 | Shimoda et al. | |
| 2004/0192082 A1 | 9/2004 | Wagner et al. | |
| 2007/0123001 A1 | 5/2007 | Reis | |
| 2007/0230103 A1 | 10/2007 | Baumann et al. | |
| 2008/0012121 A1 | 1/2008 | Hara | |
| 2008/0110017 A1 | 5/2008 | Hara | |
| 2008/0257589 A1 | 10/2008 | Ostmann et al. | |
| 2009/0158232 A1 | 6/2009 | Ronkka et al. | |
| 2009/0283891 A1 | 11/2009 | Dekker et al. | |

FOREIGN PATENT DOCUMENTS

| | | |
|---|---|---|
| EP | 2066159 A1 | 6/2009 |
| EP | 2200412 A1 | 6/2010 |
| GB | 2313713 A | 12/1997 |
| JP | H06-350225 A | 12/1994 |
| JP | 2001-135910 A | 5/2001 |
| JP | 2004-281738 A | 10/2004 |
| JP | 2004-342700 A | 12/2004 |
| JP | 2008-124387 A | 5/2008 |
| WO | 03/010825 A1 | 2/2003 |
| WO | 03021679 A2 | 3/2003 |
| WO | 2004014657 A2 | 2/2004 |
| WO | 2008/102866 A1 | 8/2008 |
| WO | 2009033728 A2 | 3/2009 |
| WO | 2009070018 A1 | 6/2009 |
| WO | 2010000225 A1 | 1/2010 |
| WO | 2010002252 A1 | 1/2010 |

OTHER PUBLICATIONS

International Search Report—PCT/NL2011/050092—mailing Date: Jun. 20, 2011.

Stretchable Electronic Systems. T Löher, et al, IEEE, Proc. 2006 Electronics Packaging Technology Conference, 271.

* cited by examiner

COMPONENT PLACEMENT ON FLEXIBLE AND/OR STRETCHABLE SUBSTRATES

CROSS-REFERENCE TO RELATED APPLICATIONS

This application is a U.S. National Stage application under 35 U.S.C. §371 of International application PCT/NL2011/050092 (published as WO 2011/099851 A1), filed Feb. 9, 2011 which claims priority to Application EP 10153105.1, filed Feb. 9, 2010. Benefit of the filing date of each of these prior applications is hereby claimed. Each of these prior applications is hereby incorporated by reference in its entirety.

The invention relates to a method and a system for component placement on flexible and/or stretchable substrates.

DESCRIPTION OF PRIOR ART

The placement and connection of many discrete electrical components on flexible or stretchable carriers for e.g. high density applications is a difficult, time consuming affair. Also, this is not easily implemented in a roll to roll process.

On the other hand, foil based devices show only limited flexibility and are not intrinsically stretchable. This means they may need to be cut into pieces and connected to a carrier in order to allow for a highly flexible or stretchable application.

Manufacturing methods and devices for embedding of conducting material in a stretchable substrate are known. For example, a stretchable substrate is provided on a sacrificial layer. For the purpose of the present invention, a stretchable substrate is a substrate which is stretchable, which can stretch under certain influences as forces as for instance physical or mechanical force, without thereby losing its essential functionalities. A substrate can comprise metal lines, interconnect lines, electronic components, chips etc. All the constituents together form a composite substrate. Such a composite substrate is flexible if it has at least some flexibility in at least part of it. As the method and the device made by this method are closely related, they will be described together.

The present invention furthermore relates to the field of mechanically assembling multi-foil systems, i.e. flexible laminated electronic or optic systems. In a particular type of these multi-foil systems, the so-called 'systems-in-foil', each foil may have a certain electric or optic function, like a display function, a battery function or a solar panel function. Systems-in-foil have numerous applications, e.g. in the fields of lighting and reusable and disposable sensor devices.

These foils may be made in large sizes and quantities at low costs, e.g. using production processes such as presently used in the paper printing industry. The foils may be manufactured on different locations and the system may be assembled on a central location.

In one aspect the invention aims to provide a simple roll-to-roll compatible and cost effective mass placement of discrete foil based devices on flexible and/or stretchable carriers.

DISCLOSURE OF THE INVENTION

According to one aspect, the invention provides a method of placement of a component on a stretchable substrate, comprising the steps of providing a base substrate having a stretchable substrate layer, providing a flexible foil comprising an integral arrangement of a multiple of flexible foil components; the flexible foil components each comprising component pads for electro/optical access to the flexible foil components, providing in plane interconnecting traces on the stretchable substrate layer in correspondence with the component pads in the integral arrangement; aligning the base substrate and the flexible foil so as to be used in a reel based manufacturing process; providing, through lamination of the base substrate and the flexible foil an electro/optical via connection between the traces and the component pads of the integral component arrangement; and mechanically separating the integral arrangement of flexible foil components to provide a multiple of mechanically separated components from each other to arrange an electro/optical interconnected component system on a stretchable substrate layer One advantage of the invention is that it may be used in a conventional manufacturing process for multi-foil systems such as a roll to roll, roll to sheet or sheet to roll process. The present invention will become more readily apparent from the following detailed description of the preferred embodiments of the present invention taken in conjunction with the accompanying drawings.

DESCRIPTION OF THE EMBODIMENTS

The invention concerns a method of placement of a component on a stretchable substrate. The component is manufactured as a so-called functional foil device that may be used in multi-foil systems according to the invention. Such devices may be indicatively characterized as 'a flexible laminated electronic or optic foil device'. Typically, such a functional foil device comprises at least one electrical and/or optical, in the remainder indicated as electro/optical, functional circuit. Further, typically, the functional foil system comprises at least one connection pad being connected to the at least one functional circuit. Thus, a functional foil may be considered a multi-layer device in itself.

Typical examples of such foils can be found in the following prior art publication:

1. M. Koetse et al., 'An in-plane optical sensor', Proceedings of SPIE—The International Society for Optical Engineering, vol. 6739, 2007, and In the remainder, functional foils are also generally referenced as 'foil'. These foil devices are not stretchable in the common sense of the word, because typically the foil substrates of these devices such as polyimide or PEN, when subject to already very low stretching forces, will disintegrate whereas its electro/optic functionality is almost immediately lost when the device is subject to stretching. Typically, substrates used for such devices cannot be stretched more then 10% of the area, whereas a stretchability is desired, for the stretchable carrier in the order of at least more than 200% area enlargement.

Figure 1:
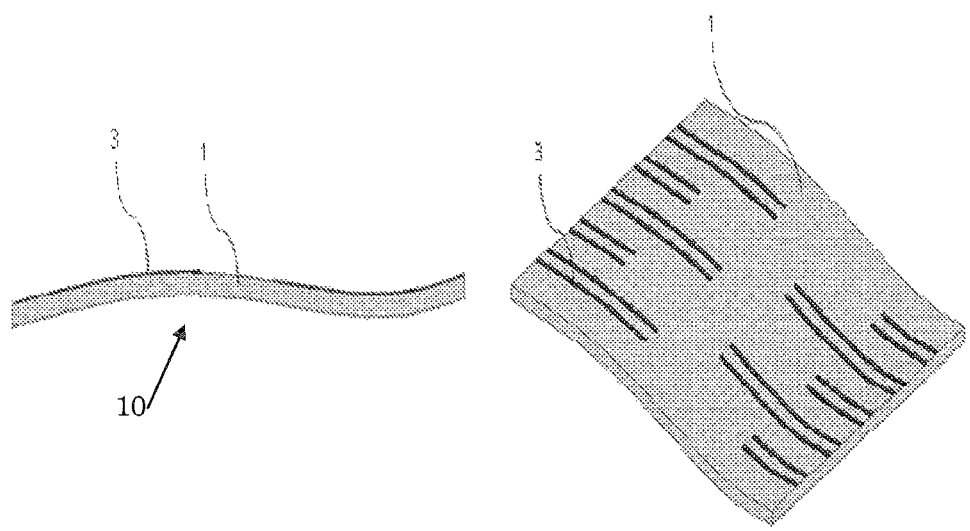
FIG. 1 shows a first manufacturing step of the manufacturing method.

In more detail, FIG. 1 shows a first manufacturing step of the manufacturing method. A base substrate 10 is provided having a stretchable substrate layer 1 (hereafter also indicated as stretchable carrier 1) and that contains electrical contact paths and/or tracks 3. These will be used for driving and/or reading out of the functional components 2 (see subsequent Figures). Examples of stretchable substrates are disclosed in EP1746869 wherein after removal of a sacrificial layer, additional sets of components can be introduced on the stretchable substrate. Alternatively, a textile having conductive tracks (conductive yarn) arranged can be provided. While the invention relates to a method of placement of a component on a stretchable substrate 1, during production, a sacrificial substrate (not shown) may include a non-stretchable sacrificial layer. Accordingly, a base substrate 10 is provided having a stretchable substrate layer 1 and optionally, said base substrate comprises a non-stretchable sacrificial layer which is removed after lamination. In addition, the stretchable substrate layer comprises in plane interconnecting traces 3 in correspondence with component pads to be placed thereon.

Figure 2:
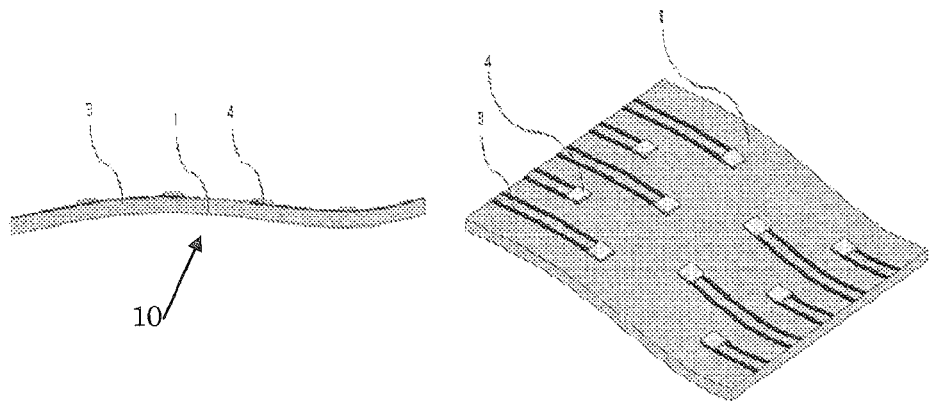
FIG. 2 shows a subsequent manufacturing step of the manufacturing method.

FIG. 2 shows a subsequent manufacturing step of the manufacturing method, wherein an adhesive layer 4 is applied specifically on those places where devices or components 2 need to be placed. This can be done in various ways. For example, the adhesive 4 may be printed or applied with some other patterned method, or it may be prepatterned and transferred via a release liner (not shown). Accordingly, on a stretchable or highly flexible carrier 1 with conductive tracks 3 patches 4 of a relatively stiff adhesive are applied, for instance, by printing, or by transferring a prepatterned trace pattern via e.g. a release tape. Specifically, in plane interconnecting traces 3 may be provided on the stretchable substrate layer 1 by transfer via a release liner having prepatterned traces arranged thereon.

Figure 3:
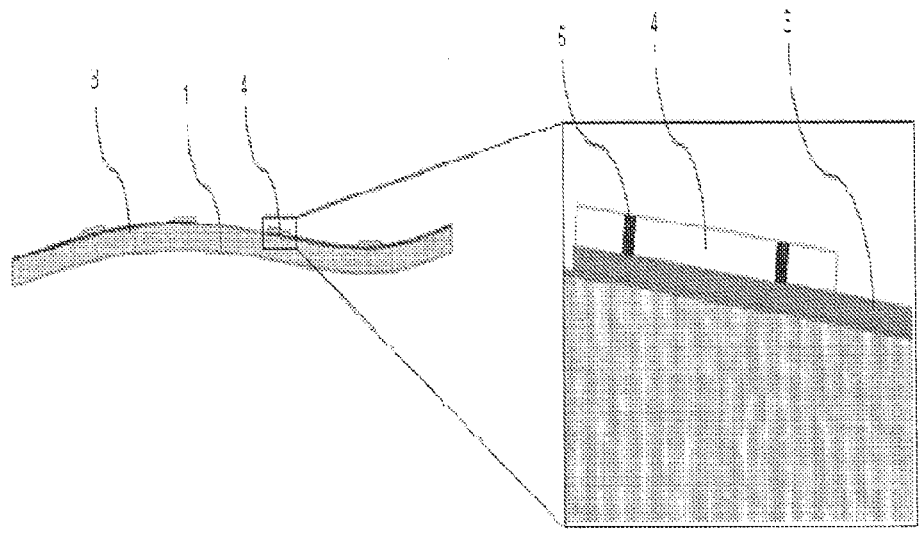
FIG. 3 shows a via forming step.

FIG. 3 shows a via forming step, wherein interconnections (vias) 5 may be provided through the adhesive layer 4. Alternatively, the vias 5 may be preformed in the adhesive layer 4, prior to providing the layer 4 on the stretchable base substrate 1.

The (cured) adhesive 4 is preferably less flexible than the carrier 1 and possibly also stiffer that the foil based component 2. Because of this mechanical stresses on the interconnections between adhesive 4 and component 2 are reduced. Interconnection can be realized via the adhesive layer 4. Alternatively, the solid state adhesive layer has convertible conductivity properties within a conversion zone, so as to form a conductive structure by thermal/foton conversion. The conductive adhesive may be of an isotropic or anisotropic nature, in a manner disclosed in PCT/NL2009/050389 and PCT/NL2008/050750 of the same applicant which are incorporated by reference.

Examples of adhesives that may be used to form the solid state adhesive layer 4 are epoxies and acrylates, but also thermoplastic polymers like ethylene-vinyl acetate (EVA) and modified polypropylenes. The thermoplastic polymers may include pressure sensitive adhesives, thermo hardening adhesives and/ thermoplastic materials and/or UV hardening adhesives. The thickness of the adhesive layer 4 may vary in the order of 5-50 micrometers.

Figure 4:
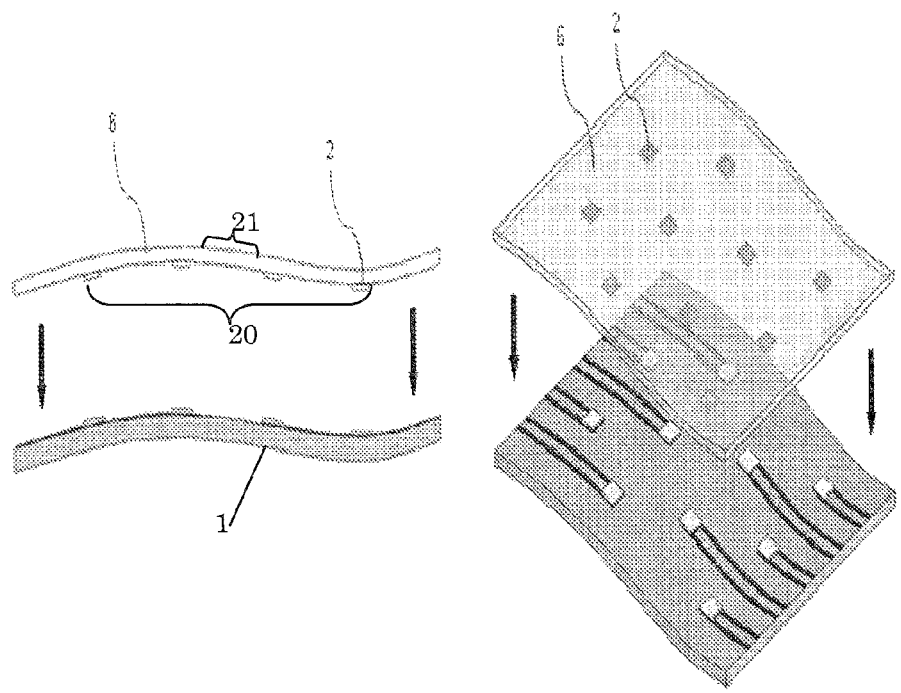
FIG. 4 shows an alignment step.

FIG. 4 shows an alignment step. In this step, the carrier 1 and a flexible foil 6 are aligned so as to be used in a reel based manufacturing process. Examples of such reel based alignment are disclosed in European Patent application no. 08152794 of the same applicant, herein incorporated by reference. The flexible foil 6 comprises an integral arrangement 20 of a multiple of flexible foil components 2; the flexible foil 6 components each comprising component pads 7 (see FIG. 7) for electro/optical access to the flexible foil components. The integral arrangement 20 of flexible foil components 2 is defined by at least a single mechanical connection via a substrate layer or common foil between the components 2. Typically, components 2 are produced in a process wherein the common layer defines a planar substrate used to realize the component structure. Typically, the planar substrate is produced in a roll to roll process. As part of the integral arrangement 20, interconnecting zones 21 define the region between the components 2. These zones 21 do not possess device functionality and may be removed or cut for mechanical separation of the components 2. The zone 21 may be covering a substantial interdistance between or be as small as a single cut.

Figure 5:
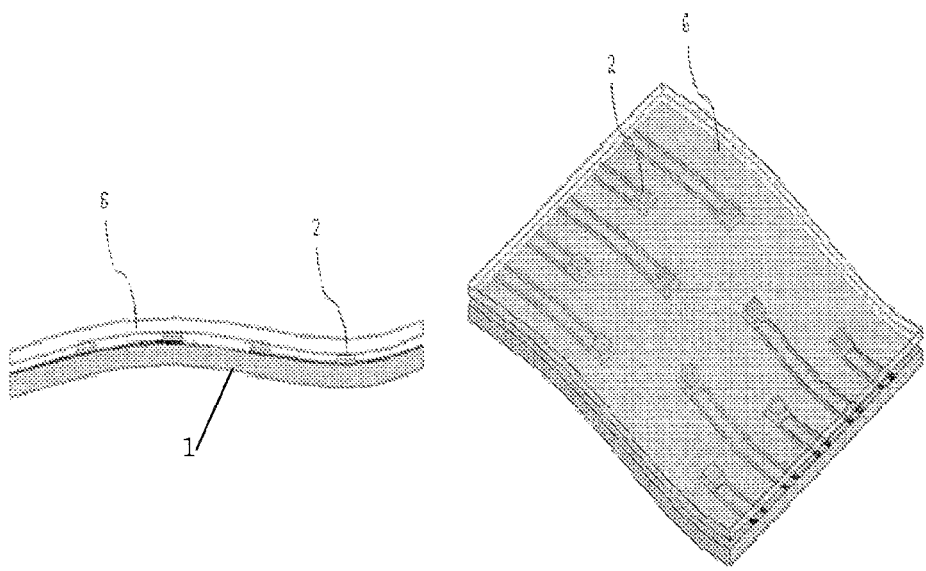
FIG. 5 shows a lamination step.

FIG. 5 shows a lamination step. Here, the foil 6 containing the components 2 is laminated to the carrier 1 with enough accuracy such that the electrical interconnection with the carrier 1 may be made. Accordingly, through lamination of the carrier 1 and the flexible foil 6 an electro/optical via connection is provided between the traces and the component pads of the integral component arrangement.

Figure 6:
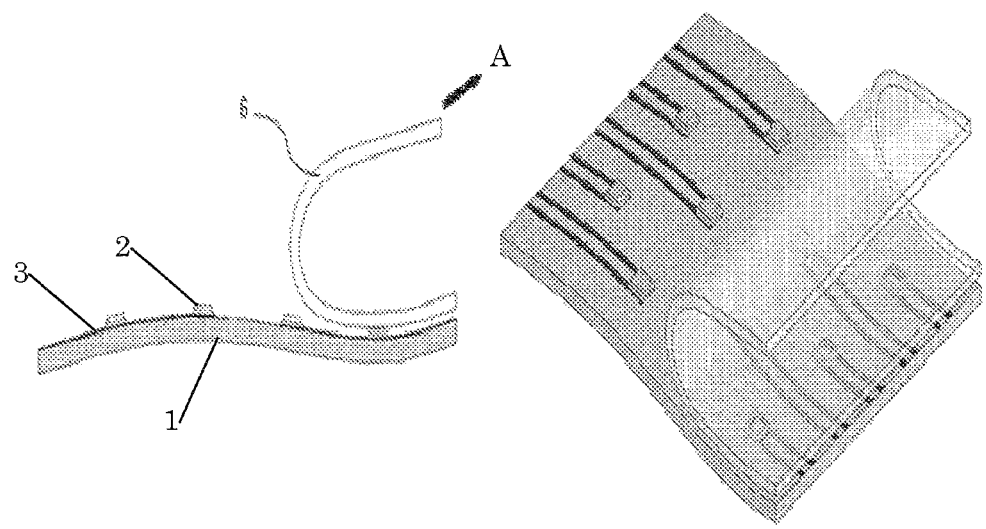
FIG. 6 shows a further manufacturing step.

FIG. 6 shows a further manufacturing step. In this step, intermediate zones 21 that do not contain any functionality may be removed (A) to regain flexibility or stretchability in the assembled system 111. This may be done in various ways. E.g.

Figure 7:
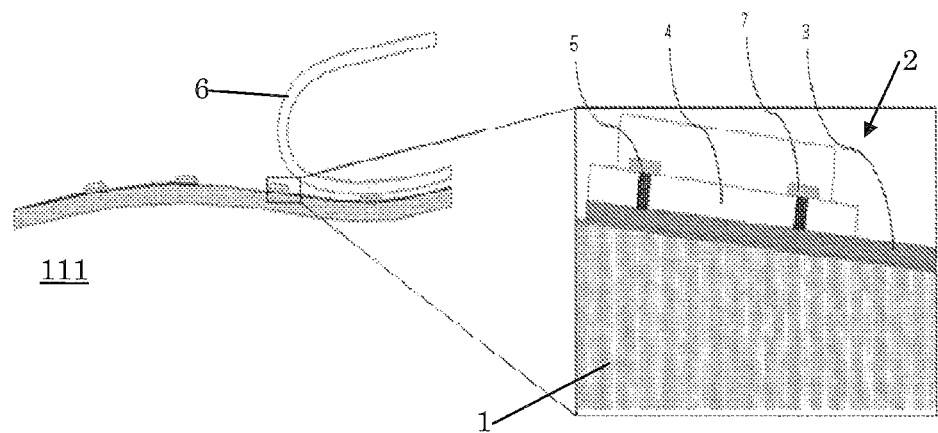
FIG. 7 shows a detailed aspect of FIG. 6 showing an electro/optical component on a stretchable substrate layer.

1) The foil 6 may be perforated before lamination. Accordingly, as an example, the integral arrangement is mechanically separated by tearing along predefined weakenings 21 in the flexible foil.
2) The foil may be laminated and the superfluous parts may be removed afterward lamination (for example by laser cutting). Thus, as an example, the integral arrangement 20 may be mechanically separated by providing a cut 21 between the foil components 2. While a single cutting trace is sufficient to provide mechanical separation, in an embodiment, the integral arrangement is mechanically separated by removing foil interconnecting zones 21 between the foil components. In these interconnection zones, additional foil devices or components may be provided in a subsequent production step.
3) As further example, PCT/NL2009/050061 of the same applicant and incorporated herein by reference, discloses a manufacturing method wherein a foil device is manufacturing separatable from a carrier substrate (as indicated in FIG. 7). A so called foilless device is manufactured on a production foil 6, the devices 2 being very thin and slightly brittle. In this case some minor mechanical stress will release material that is not adhered and connected to the surface. Accordingly, only some mechanical action may be sufficient to remove the not adhered parts, and thus, optionally, the integral arrangement may be mechanically separated by release of the flexible foil components from a foil manufacturing substrate.
4) The foil based devices 2 were pre patterned and laminated and interconnected to the carrier 1 whilst on a release liner 6.

FIG. 7 shows a detailed aspect of FIG. 6 showing an electro/optical component 2 on a stretchable substrate layer 1. Interconnection can be realized via the adhesive layer 4, for example by a process wherein electro/optical via interconnections 5 are provided in an interconnecting solid state adhesive layer 4 arranged on the stretchable substrate layer 1, the interconnecting layer 4 thus having out of plane arranged interconnections 5 in correspondence with the interconnecting traces 3. As an example, the solid state adhesive layer 4 may be provided with a conductive paste 5 arranged in through holes.

Figure 8:
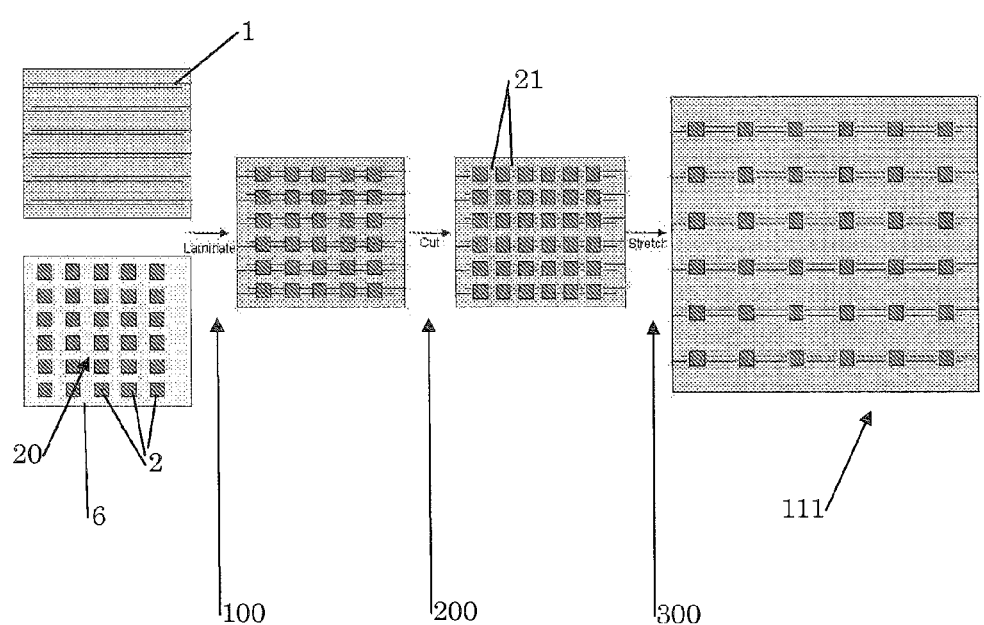
FIG. 8 shows a schematic series of steps resulting in a electro/optical interconnected component system on a stretchable substrate layer.

FIG. 8 shows a special case wherein a stretchable substrate is laminated 100, cut 200 and stretched 300:

- Laminate high density, mechanically stiff/strong device foil 6 with highly stretchable 'wired' substrate 1.
- Cut away 200 stripes of the foil not containing devices 2
- Stretch 300 wired substrate 1 to get enlarged area. Stretched areas can also be used as diffusion channel for e.g. moisture in bandage application, since device area 2 will be impenetrable but the stretchable intermediate zones may be permeable to moist (for example, by having additional perforations).

The process may be repeated for various types of devices and/or components to result in a multistack configuration or a variety of components that is planarly aligned. Accordingly, in a subsequent lamination step, a further flexible foil can be laminated with the interconnected component system on the stretchable substrate layer, the further flexible foil comprising further foil components aligned with the interconnection zones.

Alternatively, components may be fabricated on foil 6 in high density integral arrangement 20 and positioned on a stretchable carrier 1 using the above method. After cutting/release the carrier 1 may be stretched yielding a large area application with equally distributed components. This is of special interest in the fabrication of conformable sensor arrays, such as in 'smart bandage'

The extent of stretchability can be varied in between the components thereby providing a means to allocate components which are equidistantially produced (therefore more efficiently) at a predefined position on the final carrier material.

Examples of foils with different surface structures are OLED foils or organic photodiode foils (OPD). Different surface structures may prevent the foils to be melted onto each other directly. In this case, the adhesive layer may separate the foils and enables to stack two functional foils having mutually differing adjacent surface structures. Another cause for different surface structures may be a layer that is applied to a foil only locally. For example to protect OLED's against the environment, the OLED foil may be locally covered by flexible, inorganic transparent barrier layers.

The functionality of an adhesive may be enriched by providing additives to the adhesive. Optical diffuser materials may for example be added to the adhesive to improve the light guiding characteristics of the adhesive layer, e.g. to ensure a good incoupling of light from an OLED foil onto a photodiode foil. Another example of enriching an adhesive layer is by mixing water getters through the adhesive to keep water away from water-sensitive foils, like OLED foils.

The adhesive may also provide mechanical integrity to a multi-foil system. Melting foils together directly may provide insufficient coherence between the foils and cause the foil system to fall apart. An adhesive layer may provide the coherence to keep the foil system together.

Examples of the conductive material that may be used are conductive pastes like thermally or UV curing silver or copper, but also carbon-filled epoxies or acrylates. Additionally, it is possible to fill the holes with a seed-material and (electroless) grow metallic conductors from that seed.

Example 1

Smart Bandage Sensor

An example of a multi-foil system is a smart bandage sensor for in-situ monitoring of the healing of a wound. In an embodiment a polyurethane substrate (having, as an indicative value, a stretchability up to 500%) may be used as carrier for a smart bandage application. Thus, a device functionality remains intact while the stretchable area is enlarged with values of 200, 300 up to 500% of the unstretched area value.

As an example, a pulse oximeter sensor device may be manufactured having a stretchable substrate and including a plurality of reflection based OLEDs and OPDs fabricated on non-stretchable flexible foil. Typically, such flexible foils cannot be stretched more than 200% without losing its electro-optic functionality and may disintegrate already with values below 20% area enlargement.

Currently components are OLEDs and OPD but also printed passives (e.g. resistors, capacitor) or combinations of these may be placed in a similar fashion when such components are manufactured as an integral arrangement on a production foil as hereabove explained.

Figure 9:
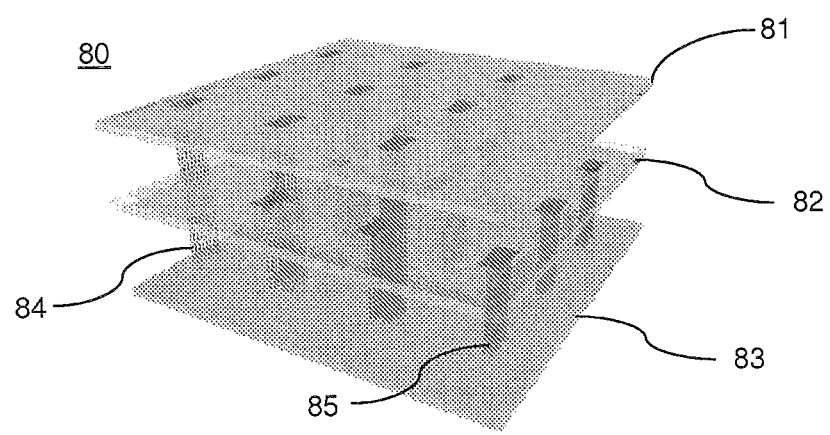
FIG. 9 shows an example product.

FIG. 9 shows the smart bandage sensor 80 as a three-foil system comprising three functional foils 81, 82 and 83. The three foils 81, 82 and 83 are laminated and electrically interconnected via two layers of adhesive. The adhesive layers between the foils are not visible in FIG. 9. First foil 81 is an 'OLED foil' comprising a Polyethylene Naphthalate (PEN) layer with printed organic light emitting diodes (OLED's). To protect the OLED's against the ambient environment, the OLED's may be locally covered by flexible, inorganic transparent barrier layers. Second foil 82 is a Photodiode foil' comprising a PEN layer with printed organic photodiodes. Like the OLED's, the photodiodes are also sensitive to environmental influences and the OLED layer may also be locally covered by flexible, inorganic transparent barrier layers. Third foil 83 is a 'Driver foil' onto which driver components are mounted. The driver foil comprises a copper layer and a polyimide layer. As is well known, a polyimide layer is not-stretchable and disintegrates at 5-25% area enlargement— whereas the electro-optical device functionality is already long lost before disintegration of the polyimide layer. Both the OLED foil 81 and the Photodiode foil 82 are electrically connected to the Driver foil 83. The sensor is manufactured by a manufacturing process as herein disclosed, in particular, according to the laminate—cutting and stretching steps 100-300. In this example, first interconnects 84 connect OLED foil 81 to Driver foil 83 and second interconnects 85 connect Photodiode foil 82 to Driver foil 83. First interconnects 85 pass through Photodiode foil 82.

The detailed drawings, specific examples and particular formulations given, serve the purpose of illustration only. The specification is understood to give explicit disclosure for any feature of a disclosed embodiment in combination with other disclosed embodiments unless stated otherwise or physically impossible. A stretchable material (e.g. silicone by spinning) can be applied, or alternatively, any stretchable material such as latex, polyurethane, all kinds of rubbers like NBR (nitrile butadiene rubber) thermoplastic elastomers (TPE). TPEs are grouped into major families based on polyolefin (TPE-O), polyester (TPE-E), polyurethane (TPE-U), polyamide (TPE-A), and polystyrene (TPE-S). Additionally, the stretchable substrate may be a stretchable textile.

Furthermore, other substitutions, modifications, changes, and omissions may be made in the design, operating conditions, and arrangement of the exemplary embodiments without departing from the scope of the invention as expressed in the appended claims.

The invention claimed is:

1. Method of producing an electro/optical interconnected component system of a plurality of non-stretchable foil device components on a stretchable substrate, comprising the steps of:
   providing a base substrate having a stretchable substrate layer;
   providing a non-stretchable flexible foil comprising an integral arrangement of a multiple of flexible foil components; the flexible foil components each comprising component pads for electro/optical access to the flexible foil components;
   providing in plane interconnecting traces on the stretchable substrate layer in correspondence with the component pads in the integral arrangement;
   aligning the base substrate and the flexible foil so as to be used in a reel based manufacturing process;
   providing, through lamination of the base substrate and the flexible foil an electro/optical via connection between the traces and the component pads of the integral component arrangement; and
   mechanically separating the integral arrangement of flexible foil components to provide a multiple of mechanically separated components from each other on the stretchable substrate layer, thereby forming an interconnected component system comprising the stretchable substrate layer and the mechanically separated components provided thereon, the interconnected component system thereby regaining stretchability without losing its electro/optical functionality.

2. Method according to claim 1 wherein the integral arrangement is mechanically separated by providing a cut in the flexible foil between the foil components.

3. Method according to claim 1 wherein the integral arrangement is mechanically separated by tearing along pre-defined weakenings in the flexible foil whereby the stretchable foil is stretched without losing its electro/optical functionality.

4. Method according to claim 1 wherein the integral arrangement is mechanically separated by removing foil interconnecting zones between the foil components.

5. Method according to claim 4, wherein, in a subsequent lamination step, a further flexible foil is laminated with the interconnected component system on the stretchable substrate layer, the further flexible foil comprising further foil components aligned with the interconnection zones.

6. Method according to claim 1 wherein the integral arrangement is mechanically separated by release of the flexible foil components from a foil manufacturing substrate.

7. Method according to claim 1 wherein in plane interconnecting traces on the stretchable substrate layer are provided by transfer via a release liner having prepatterned traces arranged thereon.

8. Method according to claim 1, wherein said base substrate comprises a non-stretchable sacrificial layer which is removed after lamination.

9. Method according to claim 1, wherein the electro/optical via interconnection is provided by an interconnecting solid state adhesive layer arranged on the stretchable substrate layer, the interconnecting layer having out of plane arranged interconnections in correspondence with the interconnecting traces.

10. Method according to claim 9, wherein the solid state adhesive layer is provided with a conductive paste arranged in through holes.

11. Method according to claim 9, wherein the solid state adhesive layer has convertible conductivity properties within a conversion zone, so as to form a conductive structure by thermal/foton conversion.

* * * * *